(12) United States Patent
Li

(10) Patent No.: US 6,931,094 B2
(45) Date of Patent: Aug. 16, 2005

(54) METHODS AND SYSTEMS FOR SMOOTHING

(75) Inventor: Jianying Li, New Berlin, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 123 days.

(21) Appl. No.: 10/683,037

(22) Filed: Oct. 10, 2003

(65) Prior Publication Data

US 2005/0078791 A1 Apr. 14, 2005

(51) Int. Cl.[7] .............................................. G01N 23/083
(52) U.S. Cl. .............................. 378/62; 378/4; 378/22; 378/901
(58) Field of Search ........................... 378/4, 8, 15, 19, 378/23, 62, 901

(56) References Cited

U.S. PATENT DOCUMENTS

| 4,442,489 | A | | 4/1984 | Wagner |
| 4,580,219 | A | | 4/1986 | Pelc et al. |
| 5,262,946 | A | * | 11/1993 | Heuscher ..................... 378/15 |
| 5,640,436 | A | | 6/1997 | Kawai et al. |
| 5,848,114 | A | | 12/1998 | Kawai et al. |
| 6,393,091 | B1 | | 5/2002 | Slack et al. |
| 6,434,214 | B1 | | 8/2002 | Kawai et al. |
| 6,459,755 | B1 | | 10/2002 | Li |
| 6,493,416 | B1 | | 12/2002 | Hsieh |
| 6,658,082 | B2 | * | 12/2003 | Okumura et al. ............. 378/19 |
| 2003/0076988 | A1 | | 4/2003 | Liang et al. |
| 2004/0071258 | A1 | * | 4/2004 | Okumura et al. ............. 378/19 |
| 2005/0008116 | A1 | * | 1/2005 | Nishide et al. ............... 378/20 |

* cited by examiner

Primary Examiner—David V Bruce
(74) Attorney, Agent, or Firm—Carl B. Horton, Esq.; Armstrong Teasdale LLP (57) ABSTRACT

A method for smoothing is described. The method includes generating original projection data, and smoothing the original projection data based on variations in a current that is synchronous with phases of motion of an object.

25 Claims, 5 Drawing Sheets

METHODS AND SYSTEMS FOR SMOOTHING

BACKGROUND OF THE INVENTION

This invention relates generally to imaging and, more particularly, to methods and systems for smoothing in imaging systems.

In computed tomography (CT) imaging systems, an x-ray source emits a fan-shaped beam toward a subject, such as a patient or a piece of luggage. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately results in the formation of an image. However, one challenge is to lessen X-ray dose for a scan and to reduce streaking artifacts or noise generated due to the lower X-ray dose.

BRIEF DESCRIPTION OF THE INVENTION

In one aspect, a method for smoothing is provided. The method includes generating original projection data, and smoothing the original projection data based on variations in a current that is synchronous with phases of motion of an object.

In another aspect, a method for smoothing is provided. The method includes generating original projection data, and smoothing the original projection data based on whether one of the values of the original projection data are above at least one threshold, where the at least one threshold is a function of a normal tube current, and wherein the normal tube current is a maximum value of all tube currents supplied during a scan.

In yet another aspect, a computer-readable medium is provided. The computer-readable medium is encoded with a program configured to generate original projection data, and smooth the original projection data based on variations in a current that is synchronous with phases of motion of an object.

In still another aspect, a computer is provided. The computer is configured to generate original projection data, and smooth the original projection data based on variations in a current that is synchronous with phases of motion of an object.

In another aspect, an imaging system is provided. The imaging system includes a radiation source, an array configured to receive radiation from the radiation source, and a controller operationally coupled to the radiation source and the array. The controller is configured to generate original projection data, and smooth the original projection data based on variations in a current that is synchronous with phases of motion of an object.

DETAILED DESCRIPTION OF THE INVENTION

Figure 1:
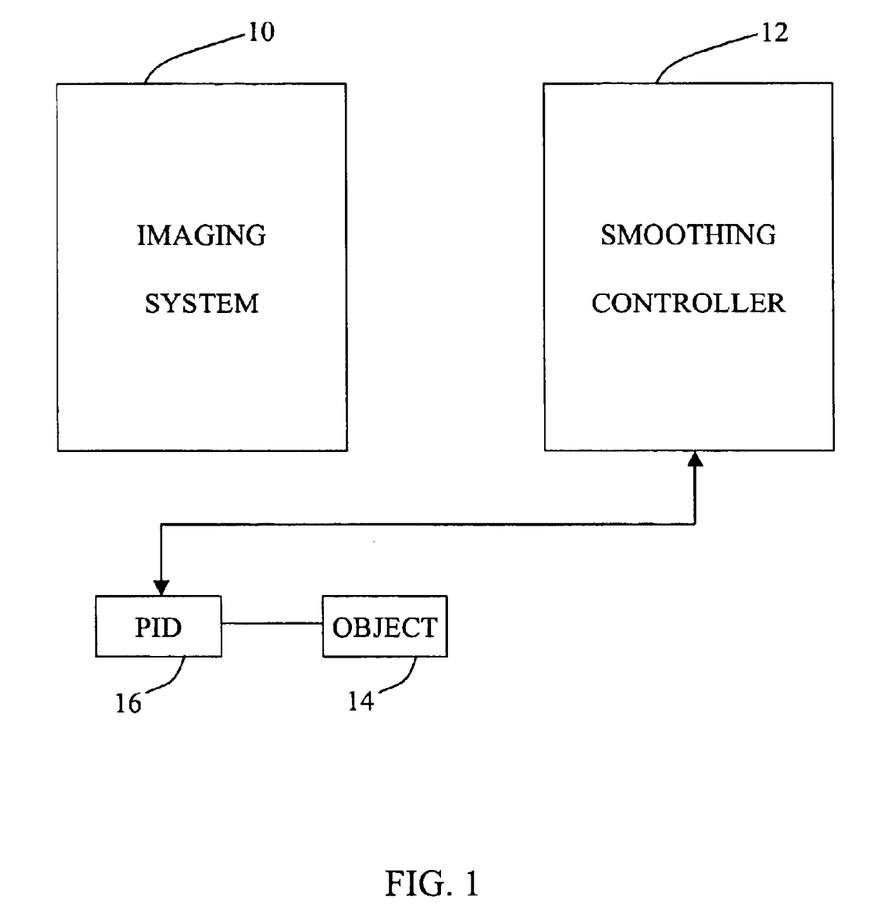
FIG. 1 is an embodiment of an imaging system in which systems and methods for smoothing are implemented.

FIG. 1 is an embodiment of an imaging system 10 in which systems and methods for smoothing are implemented. Examples of imaging system 10 include an ultrasound imaging system, magnetic resonance imaging (MRI) system, single photon emission computed tomography (SPECT) imaging system, computed tomography (CT) imaging system, and positron emission tomography (PET) imaging system. A smoothing controller 12 can be included within or located outside imaging system 10. The term controller, as used herein, is not limited to just those integrated circuits referred to in the art as computers, but broadly refers to processors, microcontrollers, microcomputers, programmable logic controllers, application specific integrated circuits, and other programmable circuits, and these terms are used interchangeably herein. Imaging system 10 scans an object 14, such as a heart, a liver, or a lung, and generates original projection data. Physiological information device (PID) 16 is coupled to smoothing controller 12 and to object 14. An example of PID 16 includes an electrocardiograph that generates an electrocardiogram (EKG). PID 16 generates physiological cycle signals, such as an EKG signals or respiratory signals, including a plurality of phases, such as cardiac phases or respiratory cycle phases. Smoothing controller 12 executes a method for smoothing on the original projection data.

Figure 2:
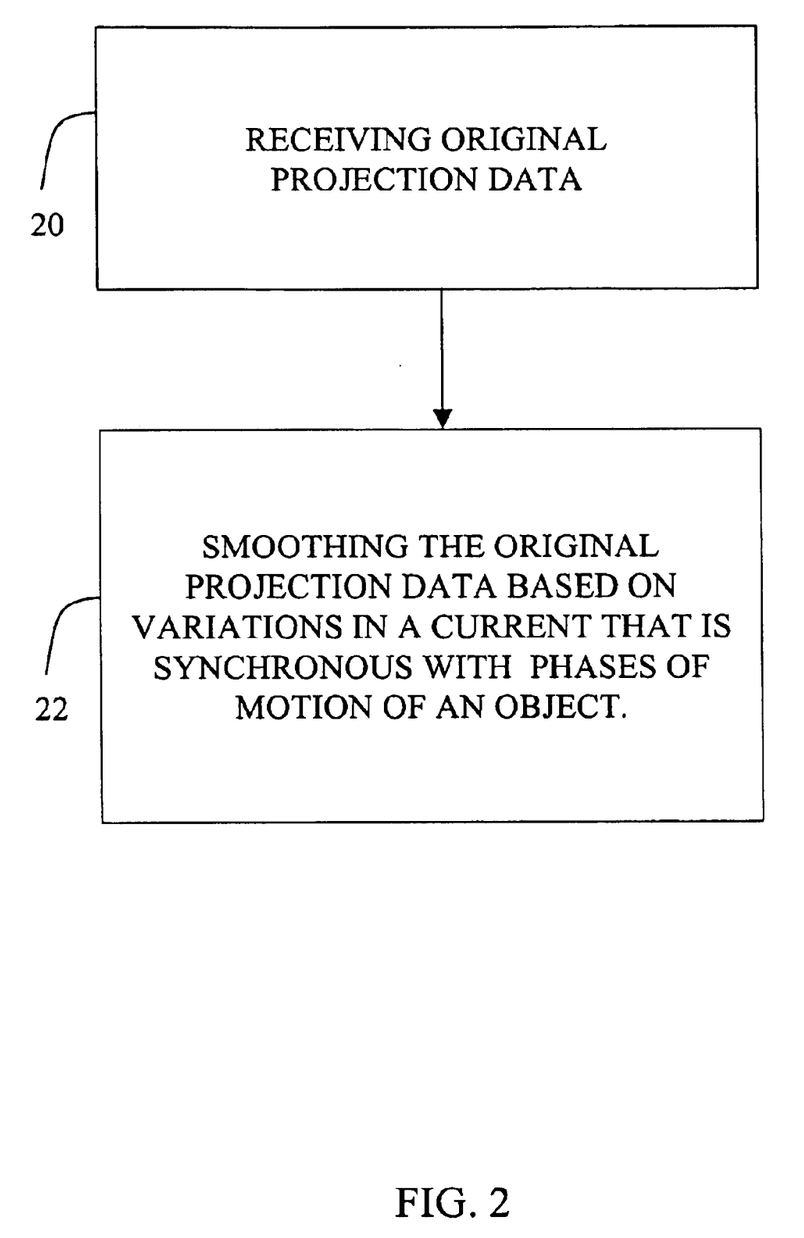
FIG. 2 is a flowchart of an embodiment of a method for smoothing.

FIG. 2 is a flowchart of an embodiment of a method for smoothing. Smoothing controller 12 receives 20 the original projection from imaging system 10. Smoothing controller 12 smoothes 22 the original projection data based on variations in a current that is synchronous with phases of motion of object 14.

In CT imaging system configurations, an X-ray source projects a fan-shaped beam which is collimated to lie within an X-Y plane of a Cartesian coordinate system and generally referred to as an "imaging plane". The X-ray beam passes through a subject, such as a patient, being imaged. The beam, after being attenuated by the subject, impinges upon an array of radiation detectors. The intensity of the attenuated radiation beam received at the detector array is dependent upon the attenuation of an X-ray beam by the subject. Each detector element of the array produces a separate electrical signal that is a measurement of the beam intensity at the detector location. The intensity measurements from all of the detectors are acquired separately to produce a transmission profile.

In third generation CT systems, the X-ray source and the detector array are rotated with a gantry within the imaging plane and around the subject to be imaged such that the angle at which the X-ray beam intersects the subject constantly changes. A group of X-ray attenuation measurements, i.e., projection data, from the detector array at one gantry angle is referred to as a "view". A "scan" of the subject includes a set of views made at different gantry angles, or view angles, during one revolution of the X-ray source and detector. Examples of a scan include an axial scan, a cine scan, and a helical scan.

In an axial scan, the projection data are processed to construct an image that corresponds to a 2-dimensional (2D) slice taken through the subject. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data are weighted according to a helical weighing factor, which is a function of both the gantry angle and detector angle. The weighted data are then processed to generate CT numbers and to construct an image that corresponds to a two dimensional slice taken through the subject.

As used herein, an element or step recited in the singular and preceded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 3:
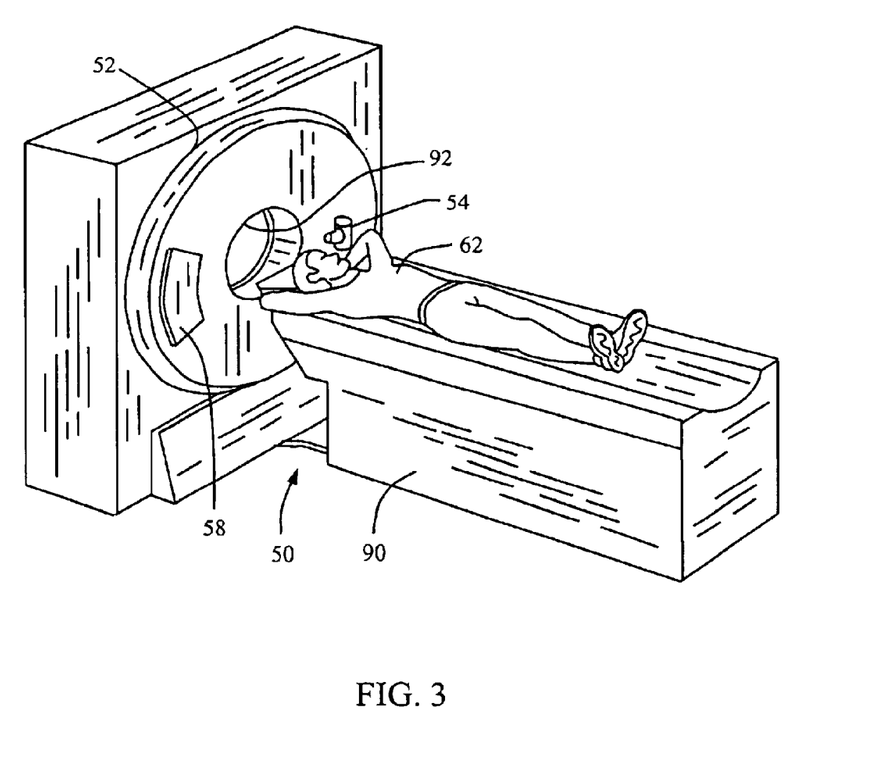
FIG. 3 is a perspective an embodiment of a computed tomography (CT) system in which systems and methods for smoothing are implemented.
Figure 4:
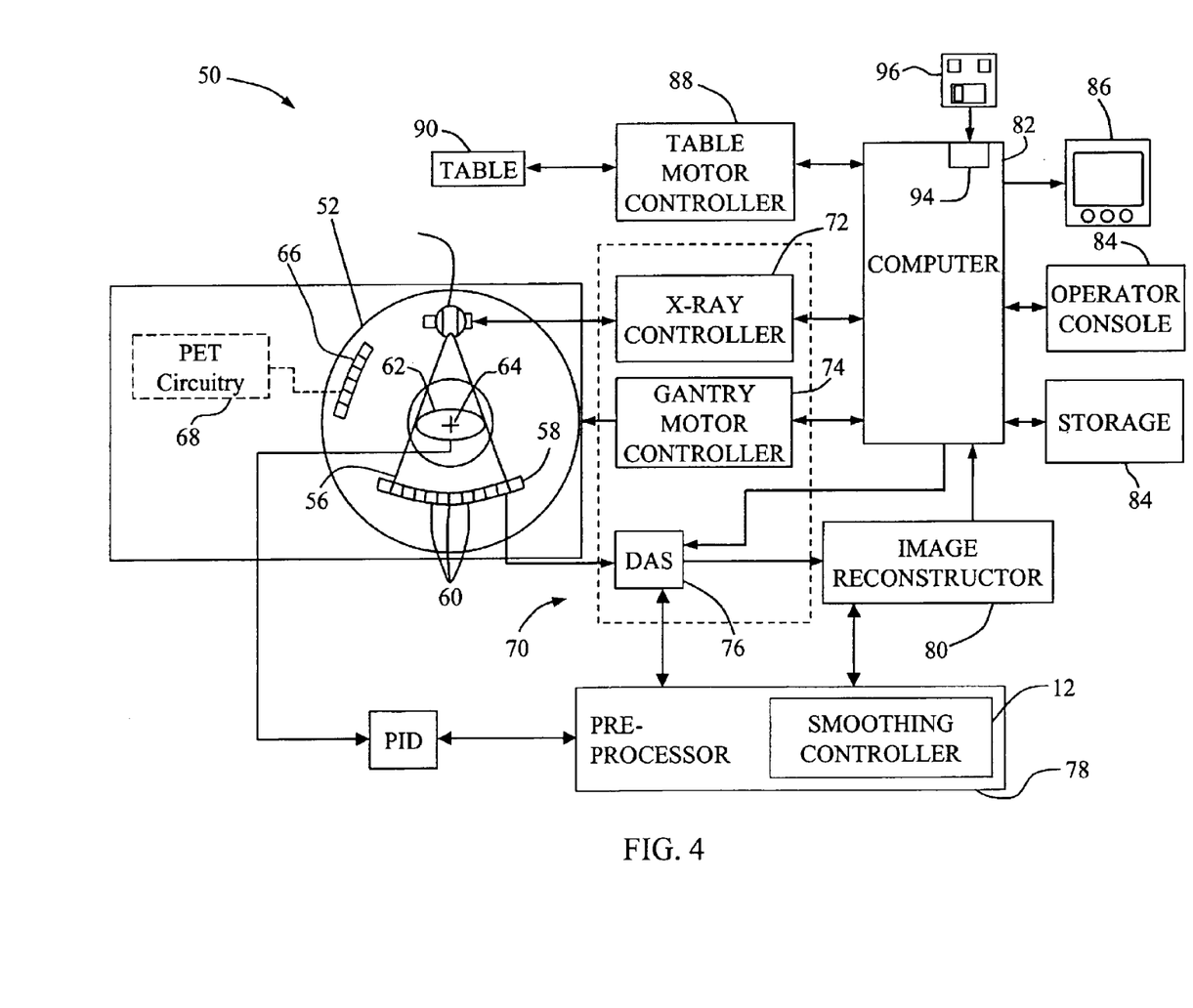
FIG. 4 is a block diagram of the CT system of FIG. 3.

Referring to FIGS. 3 and 4, a multi-slice scanning imaging system, for example, a CT imaging system 50, is shown as including a gantry 52 representative of a "third generation" CT imaging system. Gantry 52 includes an X-ray source 54. When a tube current, such as a normal tube current or a lower tube current, is supplied to X-ray source 54, X-ray source 54 projects a beam of X-rays 56 toward a detector array 58 on the opposite side of gantry 52. The normal tube current is a maximum amount of tube current used for a scan and the lower tube current is a current that is less than the normal tube current. Detector array 58 is formed of a plurality of detector rows (not shown) and channels (not shown). The detector rows and channels include a plurality of detector elements 60 which together sense the projected X-rays that pass through a subject 62, such as a medical patient. Each detector element 60 produces an electrical signal that represents the intensity of an impinging X-ray beam and hence allows estimation of the attenuation of the beam as it passes through subject 62. During a scan to acquire X-ray projection data, gantry 52 and the components mounted thereon rotate about a center of rotation 64.

FIG. 4 shows a detector row of detector elements 60. However, multislice detector array 58 includes a plurality of parallel detector rows of detector elements 60 such that projection data corresponding to a plurality of quasi-parallel or parallel slices can be acquired simultaneously during a scan.

Rotation of gantry 52 and the operation of X-ray source 54 are governed by a control mechanism 70 of CT imaging system 50. Control mechanism 70 includes an X-ray controller 72 that provides power and timing signals to X-ray source 54 and a gantry motor controller 74 that controls the rotational speed and position of gantry 52. A data acquisition system (DAS) 76 in control mechanism 70 samples analog data from detector elements 60 and converts the data to digital signals for subsequent processing. A pre-processor 78 receives sampled and digitized original projection data from DAS 76 to pre-process the original projection data. In one embodiment, pre-processing includes, but is not limited to, an offset correction, a primary speed correction, a reference channel correction, an air-calibration, applying the methods for smoothing, and applying a negative logarithmic operation. In another embodiment, the original projection data are pre-processed up to the negative logarithmic operation and the methods for smoothing are applied before applying the negative logarithmic operation. Smoothing controller 12 applies the methods for smoothing on the original projection data.

CT scans provide anatomic images and functional information of object 14. Usually, phases in which object 14 has the least motion are selected to obtain the anatomic images. On the other hand, phases in which object 14 has any motion are selected to obtain the functional information. Phases are determined and selected using the physiological cycle signals. The normal tube current is supplied for the phases where the anatomic images are desired and the lower tube current is supplied for other phases to provide the functional information.

The method for smoothing that is executed by smoothing controller 12 includes selecting a set of thresholds for the phases with the normal tube current. For example, three thresholds are used:

$$Th=\exp(-thh), Tm=\exp(-thm), \text{ and } Tl=\exp(-thl), \qquad (1)$$

where thh, thm and thl are threshold indexes and are related by the following relationship:

$$thh=thm-ath, \text{ and } thl=thm+bth \qquad (2)$$

As an example, values of thh, thm, and thl range from 3 to 10. As another example, thh=6.4, thm=6.9, and thl=7.4 for the phases with the normal tube current. The parameters ath and bth are two constants. Examples of values of ath include values between 0 and 2. Examples of values of bth include values between 0 and 2. Alternatively, one or two of thresholds Th, Tm, and Tl are used in the method. In yet another alternative embodiment, more than three thresholds are used. Assuming that scans with the normal tube current produce acceptable image quality for most patients, the thresholds are selected so that the smoothing is minimum for the phases with the normal tube current. The method also includes automatically adjusting the thresholds Th, Tm, and Tl based on the tube current during a scan with variable tube currents. The thresholds are adjusted based on the following relationship.

$$thm=m+n*tm+o*tm*tm+p*tm*tm*tm, \qquad (3)$$

where tin is the ratio of the lower tube current, represented by mA_lower, at any given time to the normal tube current, represented by mA_normal, and where * represents multiplication.

$$tm=mA\_\text{lower}/mA\_\text{normal} \qquad (4)$$

Minimum and maximum values of thm can be changed if desired. Values of m, n, o, and p change with a change in the minimum and maximum values of thm. For instance, for a maximum value of thm=6.9 and a minimum value of thm=4.5, an exemplary value of m is 4.5, an exemplary value of n is 0.95, an exemplary value of o is 0.80, and an exemplary value of p is 0.65.

The original projection data are three-dimensional (3D) vectors, where a first vector provides a detector row value, a second vector provides a channel value, and a third vector provides a view angle value. For each view angle and for each detector row, there are multiple channel values, such as 888 channel values. For every view angle and detector row, a minimum value from the channel values is found and compared to the thresholds. Based on the comparison, the method includes performing one of the following operations.

(a) No smoothing if the minimum value is greater than or equal to Th,
(b) x-point smoothing if the minimum value is less than Th but greater than or equal to Tm,
(c) y-point smoothing if the minimum value is less than Tm but greater than or equal to Tl; and
(d) z-point smoothing if the minimum value is less than Tl, where x is a number less than y and y is a number less than z. An example of x is 3, an example of y is 5, and an example of z is 7. Smoothing can have different weights. For example, in 3-point smoothing, $\frac{1}{3}$, $\frac{1}{3}$, and $\frac{1}{3}$ are the weights. In the example, smoothed projection data will be $F(i)=\frac{1}{3}*f(i-1)+\frac{1}{3}*f(i)+\frac{1}{3}*f(i+1)$, where $f(i)$ is the original projection data and where * represents multiplication. As another example, 0.25, 0.50, and 0.25 are the weights for the 3-point smoothing.

After smoothing of the original projection data, the smoothed projection data are obtained. Error projection data are obtained by subtracting the smoothed projection data from the original projection data. The error projection data are modified, for instance, multiplied by a smoothing gain factor and subtracted from the original projection data to form new projection data. Examples of the smoothing gain factor include values between 0 and 1. The smoothing gain factor is a function of the original projections and is close to 1.0 when the original projection data are very small.

An image reconstructor 80 receives the new projection data from smoothing controller 12 and performs high-speed image reconstruction to reconstruct images. During the reconstruction, the set of thresholds will be adjusted automatically for different cardiac phases based on the tube currents using equations (1) through (4) to provide additional smoothing for phases that were scanned with lower tube currents. The reconstructed images are applied as an input to a computer 82 which stores the images in a mass storage device 84.

Computer 82 also receives commands and scanning parameters from an operator via a console 84 that has a keyboard. An associated cathode ray tube display 86 allows the operator to observe the reconstructed image and other data from computer 82. The operator supplied commands and parameters are used by computer 82 to provide control signals and information to DAS 76, X-ray controller 72 and gantry motor controller 74. In addition, computer 82 operates a table motor controller 88 which controls a motorized table 90 to position a patient in gantry 52. Particularly, table 90 moves portions of the patient through gantry opening 92.

In one embodiment, computer 82 includes a device 94, for example, a floppy disk drive or CD-ROM drive, for reading instructions and/or data from computer-readable medium 96, such as a floppy disk or CD-ROM. In another embodiment, computer 82 executes instructions stored in firmware (not shown). Computer 82 is programmed to perform functions described herein, and as used herein, the term computer is not limited to just those integrated circuits referred to in the art as computers, but broadly refers to processors, microcontrollers, microcomputers, programmable logic controllers, application specific integrated circuits, and other programmable circuits, and these terms are used interchangeably herein.

Although the specific embodiment mentioned above refers to a third generation CT system, methods for smoothing equally apply to fourth generation CT systems that have a stationary detector and a rotating X-ray source, and fifth generation CT systems that have a stationary detector and an X-ray source.

Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro PET and CT systems sized to study lab animals as opposed to humans.

Figure 5:
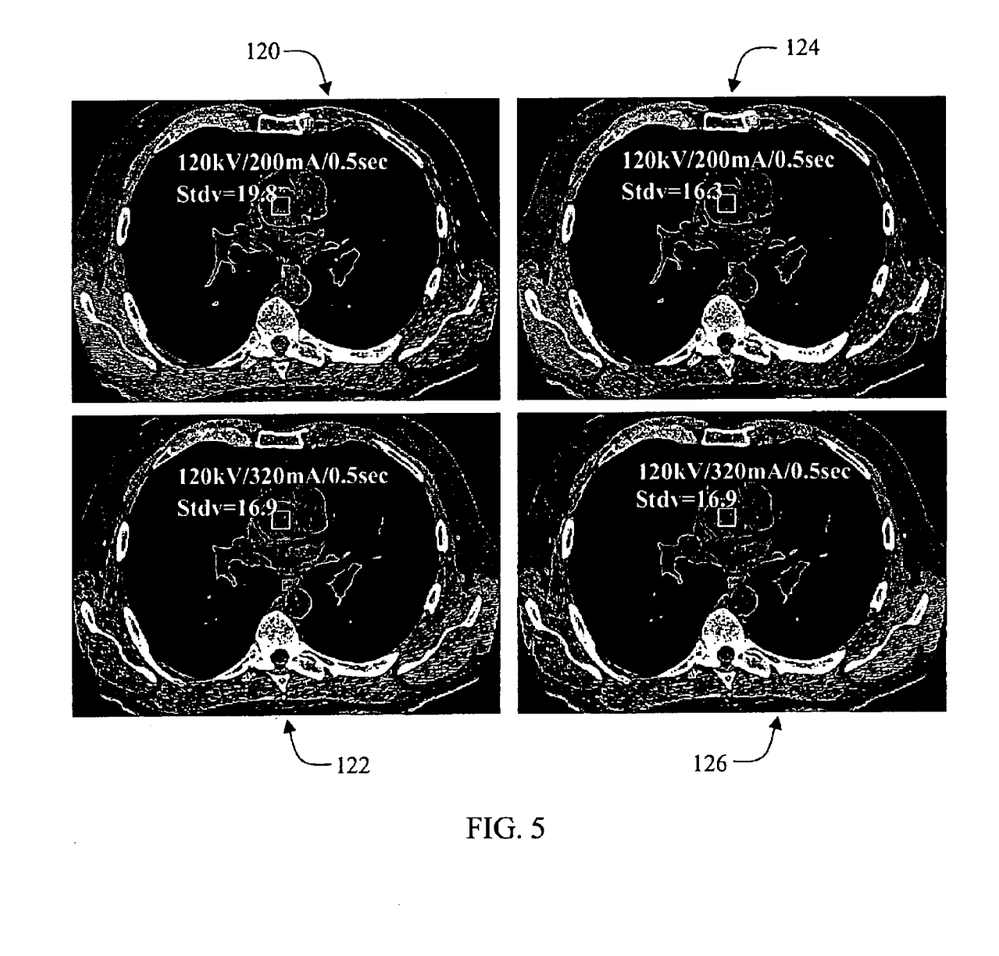
FIG. 5 shows images obtained by performing cardiac scans of patients to illustrate the effects of applying the methods for smoothing.

FIG. 5 shows images 120, 122, 124, and 126 obtained by performing cardiac scans of patients to illustrate the effects of the methods for smoothing. Images 120 and 122 are reconstructed without applying the methods for smoothing and images 124 and 126 are reconstructed after applying the methods for smoothing. Images 122 and 126 are obtained at a normal tube current of 320 milliamperes (mA) and images 120 and 124 are obtained at a lower tube current of 200 mA. By comparing images 122 and 124, the methods have a minor effect on image 122 with the normal tube current. However, by comparing images 120 and 124, the methods reduce noise and streaking artifacts in image 120 with the lower tube current while minimizing resolution loss of image 120.

Technical effects of the herein described systems and methods include reducing noise or streaking artifacts in images generated with the lower tube current. The streaking artifacts or the noise are reduced by applying a higher level of smoothing to images with the lower tube current than images with the normal tube current. The methods save energy used for scanning object 14 by applying a level of smoothing that corresponds to a tube current, which is synchronous with the phases of motion of object 14.

While the invention has been described in terms of various specific embodiments, those skilled in the art will recognize that the invention can be practiced with modification within the spirit and scope of the claims.

What is claimed is:

1. A method for smoothing comprising:
   generating original projection data having values; and
   smoothing the original projection data based on variations in a current that is synchronous with phases of motion of an object.

2. A method in accordance with claim 1 wherein smoothing the original projection data based on variations in a current that is synchronous with phases of motion of an object comprises:
   determining at least one threshold;
   determining whether one of the values of the original projection data lies below the at least one threshold; and
   determining whether one of the values of the original projection data lies above the at least one threshold.

3. A method in accordance with claim 2 wherein determining at least one threshold comprises:

determining thresholds Th=exp(−thh), Tm=exp(−thm), and Tl=exp(−thl), wherein thh, thm, and thl are threshold indexes related by thh=thm−ath, and thl=thm+bth, wherein ath and bth are constants, and wherein thm is a function of the current.

4. A method in accordance with claim 2 wherein determining at least one threshold comprises:

determining thresholds Tl=exp(−thh), Tm=exp(−thm), and Tl=exp(−thl), wherein thh, thm, and thl are threshold indexes related by thh=thm−ath, and thl=thm+bth, wherein ath and bth are constants, wherein thm is provided by thm=m+n*tm+o*tm*tm+p*tm*tm*tm, wherein m, n, o and p are constants, and wherein tm is a ratio of a lower tube current that is lower than a normal tube current.

5. A method in accordance with claim 2 wherein the at least one threshold includes a low and a high threshold, and smoothing the original projection data based on variations in a current that is synchronous with phases of motion of an object comprises:

providing a first level of smoothing if the value is below the low threshold; and providing no smoothing if the value is greater than the high threshold.

6. A method in accordance with claim 1 wherein the smoothing is performed during a pre-processing operation in a computed tomography imaging system.

7. A method in accordance with claim 1 wherein the smoothing generates smoothed projection data, and wherein the method comprises subtracting the smoothed projection data from the original projection data to obtain error projection data.

8. A method in accordance with claim 7 comprising:

modifying the error projection data by a smoothing gain factor to form modified projection data; and subtracting the modified projection data from the original projection data to form new projection data.

9. A method in accordance with claim 8 comprising reconstructing images from the new projection data.

10. A method in accordance with claim 1 wherein smoothing the original projection data based on variations in a current that is synchronous with phases of motion of an object is performed before performing a logarithmic operation.

11. A method for smoothing comprising:

generating original projection data; and smoothing the original projection data based on whether one of the values of the original projection data are above at least one threshold, wherein the at least one threshold is a function of a normal tube current, and wherein the normal tube current is a maximum value of all tube currents supplied during a scan.

12. A computer-readable medium encoded with a program configured to:

generate original projection data; and smooth the original projection data based on variations in a current that is synchronous with phases of motion of an object.

13. A computer-readable medium in accordance with claim 12 wherein to smooth the original projection data based on variations in a current that is synchronous with phases of motion of an object the program is configured to:

determine at least one threshold;

determine whether one of the values of the original projection data lies below the at least one threshold; and determine whether one of the values of the original projection data lies above the at least one threshold.

14. A computer-readable medium in accordance with claim 13 wherein to determine at least one threshold the program is configured to:

determine thresholds Th=exp(−thh), Tm=exp(−thm), and Tl=exp(−thl), wherein thh, thm, and thl are threshold indexes related by thh=thm−ath, and thl=thm+bth, wherein ath and bth are constants, and wherein thm is a function of the current.

15. A computer-readable medium in accordance with claim 13 wherein to determine at least one threshold the program is configured to:

determine thresholds Th=exp(−thh), Tm=exp(−thm), and Tl=exp(−thl), wherein thh, thm, and thl are threshold indexes related by thh=thm−ath, and thl=thm+bth, wherein ath and bth are constants, wherein thm is provided by thm=m+n*tm+o*tm*tm+p*tm*tm*tm, wherein m, n, o and p are constants, and wherein tm is a ratio of a lower tube current that is lower than a normal tube current.

16. A computer-readable medium in accordance with claim 13 wherein the at least one threshold includes a low and a high threshold, and wherein to smooth the original projection data based on variations in a current that is synchronous with phases of motion of an object the program is configured to:

provide a first level of smoothing if the value is below the low threshold; and provide no smoothing if the value is greater than the high threshold.

17. A computer-readable medium in accordance with claim 12 wherein the program is configured to smooth the original projection data in a pre-processing operation in a computed tomography imaging system.

18. A computer-readable medium in accordance with claim 12 wherein the program is configured to smooth to generate smoothed projection data, and wherein the program is configured to subtract the smoothed projection data from the original projection data to obtain error projection data.

19. A computer-readable medium in accordance with claim 18 wherein the program is configured to:

modify the error projection data by a smoothing gain factor to form modified projection data; and subtract the modified projection data from the original projection data to form new projection data.

20. A computer-readable medium in accordance with claim 19 wherein the program is configured to reconstruct images from the new projection data.

21. A method in accordance with claim 12 wherein to smooth the original projection data based on variations in a current that is synchronous with phases of motion of an object the program is configured to smooth before performing a logarithmic operation.

22. A computer configured to:

generate original projection data; and smooth the original projection data based on variations in a current that is synchronous with phases of motion of an object.

23. A computer in accordance with claim 22 wherein to smooth the original projection data based on variations in a current that is synchronous with phases of motion of an object the controller is configured to:

determine at least one threshold;

determine whether one of the values of the original projection data lies below the at least one threshold; and determine whether one of the values of the original projection data lies above the at least one threshold.

24. An imaging system comprising:

a radiation source;

an array configured to receive radiation from the radiation source; and a controller operationally coupled to the radiation source and the array, the controller configured to:

generate original projection data; and smooth the original projection data based on variations in a current that is synchronous with phases of motion of an object.

25. An imaging system in accordance with claim 24 wherein to smooth the original projection data based on variations in a current that is synchronous with phases of motion of an object the controller is configured to:

determine at least one threshold;

determine whether one of the values of the original projection data lies below the at least one threshold; and determine whether one of the values of the original projection data lies above the at least one threshold.

* * * * *

UNITED STATES PATENT AND TRADEMARK OFFICE
CERTIFICATE OF CORRECTION

PATENT NO. : 6,931,094 B2
APPLICATION NO. : 10/683037
DATED : August 16, 2005
INVENTOR(S) : Li It is certified that error appears in the above-identified patent and that said Letters Patent is hereby corrected as shown below:

In Claim 4, column 7, line 10, delete "Tl=exp(-thh)" and insert therefor
-- Th=exp(-thh) --.

Signed and Sealed this

Thirtieth Day of October, 2007

JON W. DUDAS
*Director of the United States Patent and Trademark Office*